United States Patent [19]

Romer et al.

[11] Patent Number: 5,488,051
[45] Date of Patent: Jan. 30, 1996

[54] SUBSTITUTED 5,6-DIHYDRO-5-OXO-1,4-DITHIINO-(2,3-D)-PYRIDAZINE-2,3-DICARBONITRILES, COMPOSITIONS CONTAINING THEM AND THEIR USE AS ANTIMICROBIALS

[75] Inventors: Duane R. Romer; R. Garth Pews; Ravi B. Shankar, all of Midland; Charles A. Wilson, Skandia, all of Mich.

[73] Assignee: The Dow Chemical Company, Midland, Mich.

[21] Appl. No.: 230,590

[22] Filed: Apr. 21, 1994

[51] Int. Cl.⁶ .......................... A61K 31/50; C07D 495/04
[52] U.S. Cl. ........................... 514/248; 544/235; 544/239
[58] Field of Search ........................... 544/235, 248

[56] References Cited

U.S. PATENT DOCUMENTS

| | | | |
|---|---|---|---|
| 3,761,475 | 9/1973 | Kurihara et al. | 544/345 |
| 3,825,548 | 7/1974 | Kurihara et al. | 546/80 |
| 3,829,425 | 8/1974 | Kurihara et al. | 546/114 |
| 3,843,644 | 10/1974 | Kurihara et al. | 544/345 |
| 3,845,068 | 10/1974 | Kurihara et al. | 544/235 |
| 3,849,415 | 11/1974 | Kurihara et al. | 544/235 |
| 4,147,784 | 4/1979 | Wilson | 514/248 |
| 4,150,130 | 4/1979 | Wilson | 514/248 |
| 4,172,133 | 10/1979 | Wilson et al. | 514/250 |
| 4,199,581 | 4/1980 | Mixan et al. | 514/250 |
| 4,210,645 | 7/1980 | Wilson et al. | 514/250 |

OTHER PUBLICATIONS

K. Dury, Angew. Chem. Intern. Ed. Engl. 1965, 4, 292–300.
W. E. Hahn et al., "Reaction of dimercaptomaleic acid derivatives." . . . Lodz. Towarz. Nauk, Wydzial III, Acta Chim. 10, 31–8 (1965).
A. Pollak et al., "Synthesis of pyridazine derivatives III Formation of bicyclic heterocyclic systems", Tetrahedron 21(6), 1323–6 (1965).

W. Wolf et al., "Dicyanodithiacyclohexene, a new heterocyclic nitrile for the preparation of phthalocyanines", Angew. Chem. 72, 963–6 (1960).
H. R. Schweizer, "Derivatives of 5,6–dihydro–p–dithiin–2, 3–dicarboxylic anhydride II. N–Aminoimides and cyclic hydrazides", Helv. Chim. Acta, 1969, 52(8), 2236–44.
W. E. Hahn et al., "Reactions of dimercaptomaleic acid derivatives.X. Synthesis of 3–acetyl . . . ", Lodz. Tow. Nauk. Wydz III, Acta Chim. 1970, 15, 85–90.
O. Wolniak et al., "Reactivity of 1,2–dimercapto–maleonitriles", Pharmazie, 1970, 25(10) 602–6.

Primary Examiner—Emily Bernhardt
Attorney, Agent, or Firm—S. Preston Jones; James M. Pelton

[57] ABSTRACT

Substituted 5,6-dihydro-5-oxo-1,4-dithiino-(2,3-d)-pyridazine-2,3-dicarbonitriles are prepared which correspond to the formula:

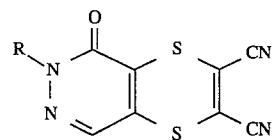

wherein R represents

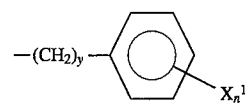

wherein $X^1$ is Cl, Br, $NO_2$ or $CH_3$, y is 0 or 1 and n is 0, 1 or 2.

These compounds have been found to exhibit antimicrobial and marine antifouling activity in industrial and commercial applications and compositions containing these compounds are so employed.

11 Claims, No Drawings

SUBSTITUTED 5,6-DIHYDRO-5-OXO-1,4-DITHIINO-(2,3-D)-PYRIDAZINE-2,3-DICARBONITRILES, COMPOSITIONS CONTAINING THEM AND THEIR USE AS ANTIMICROBIALS

FIELD OF THE INVENTION

The present invention is directed to substituted pyridazine compounds, compositions containing said compounds and the use of these compositions as antimicrobial and marine antifouling agents.

BACKGROUND OF THE INVENTION

U.S. Pat. No. 4,147,784 discloses antimicrobials for the control of bacteria and fungi and teaches the preparation and the antimicrobial use of 4,5-dihydro-4-oxo-1,3-dithiolo-(4,5-d)-pyridazine-2-ylidenepropanedinitrile compounds corresponding to the formula:

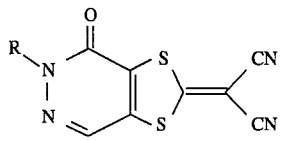

wherein R is H, an alkyl group having from 1 to about 7 carbon atoms, or

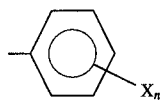

wherein X is Cl or Br and n is 0, 1 or 2.

U.S. Pat. No. 4,150,130 discloses antimicrobials for the control of bacteria and fungi and teaches the preparation of substituted 5,6-dihydro-5-oxo- 1,4-dithiino-(2,3-d)-pyridazine-2,3-dicarbonitriles corresponding to the formula:

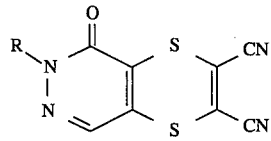

wherein R is H or an alkyl group having from 1 to about 7 carbon atoms.

While the above compounds are somewhat active, it is still desirable to identify or discover new antimicrobial and/or marine antifoulant agents. New agents are desired for several reasons; these include, but are not limited to, responding to the problem created by microbe strains developing resistance to known agents, the occurrence of undesirable interactions of certain known agents with the medium or product in which the agent is used, and high toxicity of certain known agents to certain non-target organisms such as mammals.

The present invention discloses new compounds which have high activity as an antimicrobial and/or a marine antifoulant agent.

SUMMARY OF THE INVENTION

The present invention is directed to substituted 5,6-dihydro-5-oxo-1,4-dithiino-(2,3-d)-pyridazine-2,3-dicarbonitrile compounds corresponding to the formula:

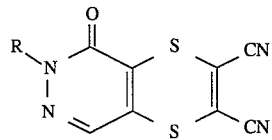

Formula I wherein R represents

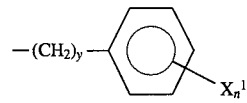

wherein $X^1$ is Cl, Br, $NO_2$ or $CH_3$, y is 0 or 1 and n is 0, 1 or 2.

The present invention is also directed to a antimicrobial composition comprising an inert diluent and an antimicrobially-effective amount of a compound corresponding to Formula I.

The present invention is further directed to a method for inhibiting microorganisms present in a microbial habitat which comprises contacting said microbial habitat with an antimicrobial composition comprising an inert diluent and an antimicrobially-effective amount of a compound corresponding to Formula I.

The antimicrobial composition of the present invention can also be employed to treat surfaces exposed to a marine environment in which marine organisms grow to prevent the growth of said marine organisms on said surfaces.

DETAILED DESCRIPTION OF THE INVENTION

The compounds of the present invention may be prepared by the reaction of an appropriately substituted 4,5-dihalo-3(2H)-pyridazinone reactant with disodium dimercaptomaleonitrile. The general scheme for this reaction is as follows:

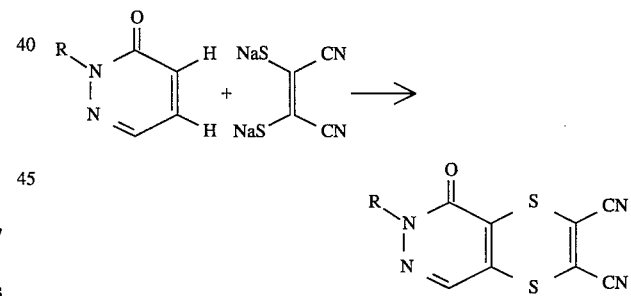

The substituted pyridazinone reactant is a compound of the formula:

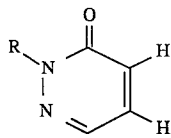

wherein R represents

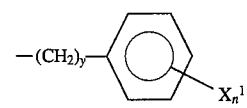

wherein $X^1$, y and n are as hereinbefore defined and H is bromo, chloro, and fluoro. The substituted 4,5-dihalo-3(2H)-pyridazinone precursor can be prepared by the reaction of an appropriately substituted hydrazine with mucochloric acid and is described in the art, such as in K. Dury, *Angew. Chem. Intern. Ed. Engl.* 1965, 4, 292.

The disodium dimercaptomaleonitrile reactant is well known and is generally disclosed in U.S. Pat. Nos. 3,761,475; 4,172,133; 4,199,581 and 4,210,645.

In carrying out these reactions, the appropriately substituted 4,5-dihalo-3(2H)-pyridazinone reactant and the disodium dimercaptomaleonitrile are typically mixed together in substantially equimolar amounts.

The reactions are typically carried out at room temperature under an ambient pressure of an inert gas in the presence of a polar, aprotic solvent, such as dimethylformamide or dimethylsulfoxide. Typically, the reactants may be added to the reaction mixture in any order of addition; they can be added neat or as a solution in the solvent used for the reaction. Subsequent to the addition of the reaction reagents, the reaction mixture will typically be maintained at a temperature of between about 25° C. to about 60° C. for a period of from about 1 to about 24 hours. The desired reaction product is typically isolated from the reaction mixture by adding a 3 to 10 volume excess of water which will precipitate the desired product. Filtration followed by washing and drying yields the desired compounds of the present invention.

The following examples illustrate the present invention and the manner by which it can be practiced but, as such, should not be construed as limitations upon the overall scope of the same.

EXAMPLE 1

Preparation of 5,6-Dihydro-5-oxo-6-phenyl-1,4-dithiino(2,3-d)pyridazine-2,3-dicarbonitrile

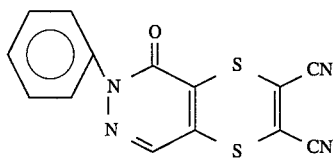

To a solution of 2.0 grams (g), 0.0083 mol. of 4,5-dichloro-1-(phenyl)-3(2H)-pyridazinone in 80 milliliters (mL) of dimethylformamide is added, in several portions, 1.9 g, 0.010 mol. of disodium Z-1,2-dicyano-1,2-ethylenedithiolate. The resulting solution is stirred overnight at room temperature. The reaction mixture is cooled to 0° C., water (200 mL) is added dropwise, and the mixture is allowed to stand for 30 minutes. The resulting solid which precipitates is isolated by filtration, washed with water and dried, giving an orange powder.

The recovered material weighs 1.98 g (77 percent of theoretical) and melts at 186° to 188° C. The structure identity is confirmed by proton nuclear magnetic resonance spectroscopy ($^1$H NMR), carbon nuclear magnetic resonance spectroscopy ($^{13}$C NMR), infrared spectroscopy (IR) and mass spectrometry (MS).

EXAMPLE 2

Preparation of 5,6-dihydro-6-(4-methylphenyl)-5-oxo-1,4-dithiino-(2,3-d)-pyridazine-2,3-dicarbonitrile

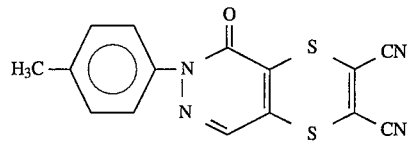

The procedure of Example 1 was followed to react 4,5-dichloro-1-(4-methylphenyl)-3(2H)-pyridazinone (1.2 g, 0.0049 mol) and disodium Z-1,2-dicyano- 1,2-ethylenedithiolate (1.4 g, 0.0074 mol) in dimethylformamide (75 mL). The recovered material weighs 1.1 g (69 percent calculated overall yield) as a dark orange powder.

EXAMPLE 3

Preparation of 5,6-dihydro-6-(4-bromophenyl)-5-oxo-1,4-dithiino-(2,3-d)-pyridazine-2,3-dicarbonitrile

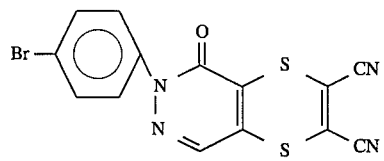

The procedure of Example 1 is followed to react 4,5-dichloro-1-(4-bromophenyl)-3(2H)-pyridazinone (1.5 g, 0.0047 mol) and disodium Z-1,2-dicyano-1,2 -ethylenedithiolate (1.3 g, 0.0072 mol) in dimethylformamide (50 mL). The recovered material weighs 1.4 (79 percent calculated overall yield) dark orange powder.

EXAMPLE 4

Preparation of 5,6-dihydro-6-(4-chlorophenyl)-5-oxo-1,4-dithiino-(2,3-d)-pyridazine-2,3-dicarbonitrile

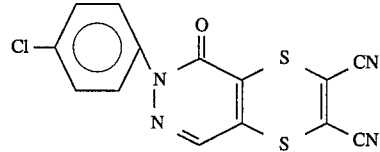

Following the procedure of Example 1, 4,5-dichloro-1-(4-chlorophenyl)-3(2H)-pyridazinone (0.61 g, 0.0022 mol) and disodium Z-1,2-dicyano- 1,2-ethylenedithiolate (0.62 g, 0.0033 mol) in dimethylformamide (50 mL) are reacted together. The recovered material weighs 0.53 g (70 percent calculated overall yield) as a bright yellow powder.

EXAMPLE 5

Preparation of 5,6-dihydro-6-(3-chlorophenyl)-5-oxo-1,4-dithiino-(2,3-d)-pyridazine-2,3-dicarbonitrile

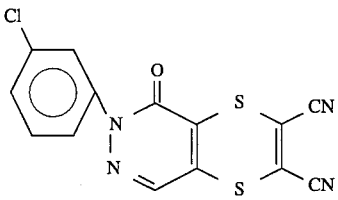

The procedure of Example 1 is followed to react 4,5-dichloro-1-(3-chlorophenyl)-3(2H)-pyridazinone (1.6 g, 0.0058 mol) and disodium Z-1,2-dicyano- 1,2-ethylenedithiolate (1.5 g, 0.0082 mol) in dimethylformamide (50 mL). The recovered material weighs 1.0 g (53 percent calculated overall yield) bright yellow powder.

EXAMPLE 6

Preparation of 5,6-dihydro-6-(3,4-dichlorophenyl)-5-oxo-1,4-dithiino-(2,3-d)-pyridazine-2,3-dicarbonitrile

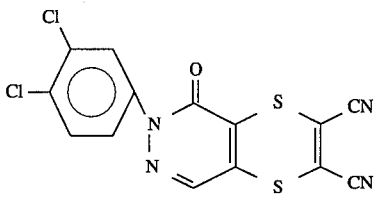

The procedure of Example 1 is followed to react 4,5-dichloro-1-(3,4-dichlorophenyl)-3(2H)-pyridazinone (0.50 g, 0.0016 mol) and disodium Z-1,2-dicyano- 1,2-ethylenedithiolate (0.42 g, 0.0023 mol) in dimethylformamide (50 mL). The recovered material weighs 0.48 g (79 percent calculated overall yield) as an orange powder.

EXAMPLE 7

Preparation of 5,6-dihydro-6-(2,4-dichlorophenyl)-5-oxo-1,4-dithiino-(2,3-d)-pyridazine-2,3-dicarbonitrile

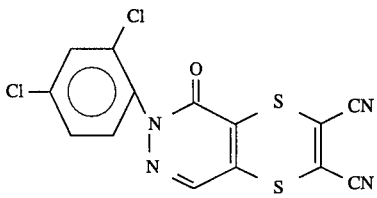

The procedure of Example 1 is followed to react 4,5-dichloro-1-(3,4-dichlorophenyl)-3(2H)-pyridazinone (0.15 g, 0.0005 mol) and disodium Z-1,2-dicyano- 1,2-ethylenedithiolate (0.12 g, 0.0006 mol) in dimethylformamide (25 mL). The recovered material weighs 0.14 g (80 percent calculated overall yield) as an orange powder.

EXAMPLE 8

Preparation of 5,6-dihydro-6-(4-nitrophenyl)-5-oxo-1,4-dithiino-(2,3-d)-pyridazine-2,3-dicarbonitrile

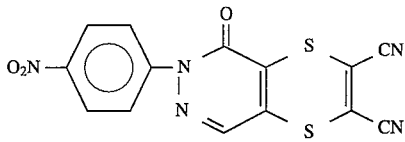

The procedure of Example 1 is followed to react 4,5-dichloro-1-(4-nitrophenyl)-3(2H)-pyridazinone (1.0 g, 0.0035 mol) and disodium Z-1,2-dicyano- 1,2-ethylenedithiolate (1.0 g, 0.0098 mol) in dimethylformamide (50 mL). The recovered material weighs 1.2 g (93 percent calculated overall yield) as a tan solid.

EXAMPLE 9

Preparation of 5,6-dihydro-6-(phenylmethyl)-5-oxo-1,4-dithiino-(2,3-d)-pyridazine-2,3-dicarbonitrile

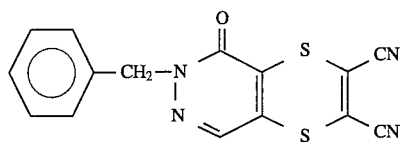

The procedure of Example 1 is followed to react 4,5-dichloro-1-(phenylmethyl).-3(2H)-pyridazinone (0.76 g, 0.0030 mol) and disodium Z-1,2-dicyano- 1,2-ethylenedithiolate (1.82 g, 0.0006 mol) in dimethylformamide (50 mL). The recovered material weighs 1.2 g (93 percent calculated overall yield) as a tan solid.

EXAMPLE 10

Preparation of 5,6-dihydro-6-((4-chlorophenyl)methyl)-5-oxo-1,4-dithiino-(2,3-d)-pyridazine-2,3-dicarbonitrile

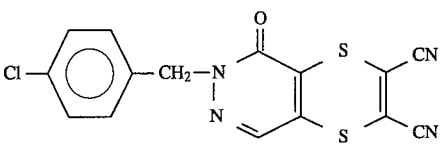

Following the procedure of Example 1, 4,5-dichloro-1-((4-chlorophenyl)methyl)-3(2H)-pyridazinone (0.41 g, 0.0014 mol) and disodium Z-1,2-dicyano-1,2-ethylenedithiolate (0.40 g, 0.0021 mol) are reacted in dimethylformamide (20 mL). The recovered material weighs 0.39 g (78 percent calculated overall yield) as a tan solid.

EXAMPLE 11

Preparation of
5,6-dihydro-6-((4-methylphenyl)methyl)-
5-oxo-1,4-dithiino-(2,3-d)-pyridazine-
2,3-dicarbonitrile

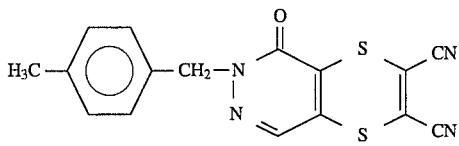

Following the procedure of Example 1, 4,5-dichloro-1-((4-methylphenyl)methyl)-3(2H)-pyridazinone (0.61 g, 0.0023 mol) and disodium Z-1,2-dicyano-1,2-ethylenedithiolate (0.63 g, 0.0034 mol) are reacted in dimethylformamide (20 mL). The recovered material weighs 0.64 g (82 percent calculated overall yield) as a tan solid.

Antimicrobial Activity

The compounds of the present invention are useful as antimicrobial additives, to provide needed antimicrobial properties, and which can be added to industrial products susceptible to microbial growth such as styrene-butadiene latexes used for paper coatings, paints, inks, adhesives, soaps, cutting oils, textiles, and paper and pigment slurries. The compounds can also be used as antimicrobial additives which are added in such personal care products as hand creams, lotions, shampoos, and hand soaps. A further advantage in the use of the compounds of the present invention is their cost-effectiveness for applications which need to have an antimicrobial continuously replenished, such as in cooling towers and pulp and paper mills.

As appreciated by those skilled in the art, not all of the compounds disclosed herein are active at the same concentrations or against the same microbial species. There may be some compound-to-compound variation in antimicrobial potency and spectrum of antimicrobial activity.

The antimicrobial compounds of the present invention may be added to formulations susceptible to microbial growth. They may be added either undiluted or dissolved in organic solvents such as glycols, alcohols, or acetone and they may also be added alone or in combination with other preservatives.

As used herein, the term "microorganism" is meant to refer to bacteria, fungi, algae, and protozoa.

As employed in the present specification and claims, the term "antimicrobially-effective amount" refers to that amount of one or a mixture of two or more of the compounds, or of a composition containing said compound or compounds, of this invention needed to exhibit inhibition of the growth of the microorganisms. Typically, the microorganism or its habitat is contacted with from about 1 part per million (ppm) to about 5,000 ppm by weight of the compound. Such amounts vary depending upon the particular compound tested and microorganism being treated. Additionally, the exact concentration of the compounds to be added in the treatment of industrial and consumer formulations may vary within a product type depending upon the components of the formulation. A preferred effective amount of the compound is from about 1 ppm to about 500 ppm, more preferably from about 1 ppm to about 50 ppm by weight, of a microbial habitat.

The term "habitat" refers to a place or site where a microorganism naturally or normally lives or grows. Typically, such a habitat will be an area that provides a moisture source, nutrient source, and/or an oxygen source such as, for example, a cooling water tower or an air washing system.

The terms "inhibition", "inhibit" or "inhibiting" refer to the suppression, stasis, kill, or any other interference with the normal life processes of microorganisms, so as to destroy or irreversibly inactivate existing microorganisms and/or prevent or control their future growth and reproduction.

The antimicrobial activity of the compounds of the present invention is demonstrated on the following compounds.

TABLE I

| Compound No. | Chemical Identity |
|---|---|
| A | 5,6-Dihydro-5-oxo-6-phenyl-1,4-dithiino-(2,3-d)-pyridazine-2,3-dicarbonitrile |
| B | 5,6-Dihydro-6-(4-methylphenyl)-5-oxo-1,4-dithiino-(2,3-d)-pyridazine-2,3-dicarbonitrile |
| C | 5,6-Dihydro-6-(4-bromophenyl)-5-oxo-1,4-dithiino-(2,3-d)-pyridazine-2,3-dicarbonitrile |
| D | 5,6-Dihydro-6-(4-chlorophenyl)-5-oxo-1,4-dithiino-(2,3-d)-pyridazine-2,3-dicarbonitrile |
| E | 5,6-Dihydro-6-(3-chlorophenyl)-5-oxo-1,4-dithiino-(2,3-d)-pyridazine-2,3-dicarbonitrile |
| F | 5,6-Dihydro-6-(3,4-dichlorophenyl)-5-oxo-1,4-dithiino-(2,3-d)-pyridazine-2,3-dicarbonitrile |
| G | 5,6-Dihydro-6-(2,4-dichlorophenyl)-5-oxo-1,4-dithiino-(2,3-d)-pyridazine-2,3-dicarbonitrile |
| H | 5,6-Dihydro-6-(4-nitrophenyl)-5-oxo-1,4-dithiino-(2,3-d)-pyridazine-2,3-dicarbonitrile |
| I | 5,6-Dihydro-6-(phenylmethyl)-5-oxo-1,4-dithiino-(2,3-d)-pyridazine-2,3-dicarbonitrile |
| J | 5,6-Dihydro-6-((4-chlorophenyl)methyl)-5-oxo-1,4-dithiino-(2,3-d)-pyridazine-2,3-dicarbonitrile |
| K | 5,6-Dihydro-5-((4-methylphenyl)methyl)-5-oxo-1,4-dithiino-(2,3-d)-pyridazine-2,3-dicarbonitrile |

The minimum inhibitory concentration (MIC) for the compounds listed in Table I is determined for 9 bacteria, using nutrient agar; and 7 yeast and fungi, using malt yeast agar. A one percent solution of the test compound is prepared in a mixture of acetone and water.

Nutrient agar is prepared at pH 6.8, representing a neutral medium, and at pH 8.2, representing an alkaline medium. The nutrient agars are prepared by adding 23 g of nutrient agar to one-liter of deionized water. In addition, the alkaline medium is prepared by adjusting a 0.04M solution of N-[tris-(hydroxymethyl)methyl]-glycine buffered deionized water with concentrated sodium hydroxide to a pH of 8.5.

Malt yeast agar is prepared by adding 3 g yeast extract and 45 g malt agar per liter of deionized water. The specific agar is dispensed in 30 mL aliquots into 25×200 mm test tubes, capped and autoclaved for 15 minutes at 115° C.

The test tubes containing the malt yeast agar and the nutrient agar are cooled in a water bath until the temperature of the agar is 48° C. Then, an appropriate amount of the one percent solution of the test compound is added (except in the controls where no compound is added) to the respective test tubes so that the final concentrations are zero (0), 1.0, 2.5, 5, 10, 25, 50, 100, 250 and 500 parts per million of the test compound in each of the respective type of agar. The contents of each of the test tubes are then transferred to separate petri plates. After drying for 24 hours, the petri plates containing nutrient agar are inoculated with bacteria and those containing malt yeast agar are inoculated with yeast and fungi.

The inoculation with bacteria is accomplished by using the following procedure. Twenty-four hour-cultures of each of the bacteria are prepared by incubating the respective bacteria in tubes containing nutrient broth for 24 hours at 30° C. in a shaker. Dilutions of each of the 24 hour-cultures are made so that nine separate suspensions (one for each of the nine test bacteria) are made, each containing $10^8$ colony forming units (CFU) per mL of suspension of a particular bacteria. Aliquots of 0.3 mL of each of the bacterial suspensions are used to fill the individual wells of Steer's Replicator. For each microbial suspension, 0.3 mL was used to fill three wells (i.e., three wells of 0.3 mL each) so that for the nine different bacteria, 27 wells are filled. The Steer's Replicator is then used to inoculate both the neutral and alkaline pH nutrient agar petri plates.

The inoculated petri plates are incubated at 30° C. for 48 hours and then read to determine if the test compound which is incorporated into the agar prevented growth of the respective bacteria.

The inoculation with the yeast and fungi is accomplished as follows. Cultures of yeast and fungi are incubated for seven days on malt yeast agar at 30° C. These cultures are used to prepare suspensions by the following procedure. A suspension of each organism is prepared by adding 10 mL of sterile saline and 10 microliters of octylphenoxy polyethoxy ethanol to the agar slant of yeast or fungi. The sterile saline/octylphenoxy polyethoxy ethanol solution is then agitated with a sterile swab to suspend the microorganism grown on the slant. Each resulting suspension is diluted into sterile saline (1 part suspension: 9 parts sterile saline). Aliquots of these dilutions are placed in individual wells of Steer's Replicator and petri plates inoculated as previously described. The petri plates are incubated at 30° C. and read after 48 hours for yeast and 72 hours for fungi.

Table II list the bacteria, yeast and fungi used in the MIC test described above along with their respective American Type Culture Collection (ATCC) identification numbers.

TABLE II

Organisms used in the Minimum Inhibitory Concentration Test

| Organism | ATCC No. |
|---|---|
| Bacteria | |
| Bacillus subtilis (Bs) | 8473 |
| Enterobacter aerogenes (Ea) | 13048 |
| Escherichia coli (Ec) | 11229 |
| Klebsiella pneumonias (Kp) | 8308 |
| Proteus vulgaris (Pv) | 881 |
| Pseudomonas aeruginosa (Pa) | 10145 |
| Pseudomonas aeruginosa (PRD-10) | 15442 |
| Salmonella choleraesuis (Se) | 10708 |
| Staphylococcus aureus (Sa) | 6538 |
| Yeast/Fungi | |
| Aspergillus niger (An) | 16404 |
| Candida albicans (Ca) | 10231 |
| Penicillium chrysogenum (Pc) | 9480 |
| Saccharomyces cerevisiae (Se) | 4105 |
| Trichoderma viride (Tv) | 8678 |
| Aureobasidium pullulan (Ap) | 16622 |
| Fusarium oxysporum (Fo) | 48112 |

In Tables III and IV, the MIC values of the compounds described in Table I as compared to the MIC values of a standard commercial preservative 1-(3-chloroallyl)-3,5,7-triaza-1-azoniaadamantane chloride is the active agent, and referred to in Tables III and IV as "STANDARD") are set forth for the bacteria organisms and yeast/fungi organisms which are listed in Table II.

TABLE III

Minimum Inhibitory Concentrations for Test Compounds in Bacteria Species (in ppm)

| Compound | | Bs | Ea | Ec | Kp | Pv | PRD | Pa | SC | Sa |
|---|---|---|---|---|---|---|---|---|---|---|
| STANDARD I | pH 6.8 | 50 | 100 | 100 | 50 | 50 | 100 | 100 | 50 | 100 |
| | pH 8.2 | 250 | 250 | 250 | 250 | 250 | 500 | >500 | 100 | 250 |
| (A) | pH 6.8 | 50 | 250 | 50 | 50 | 50 | 500 | 250 | 100 | 25 |
| | pH 8.2 | 500 | >500 | >500 | >500 | >500 | >500 | >500 | >500 | <10 |
| (B) | pH 6.8 | <10 | >500 | 50 | 50 | 500 | >500 | >500 | >500 | <10 |
| | pH 8.2 | 25 | >500 | >500 | >500 | >500 | >500 | >500 | >500 | 25 |
| (C) | pH 6.8 | <10 | >500 | 100 | >500 | 250 | >500 | >500 | 100 | >500 |
| | pH 8.2 | 100 | >500 | >500 | >500 | >500 | >500 | >500 | >500 | >500 |
| (D) | pH 6.8 | 25 | >500 | 100 | >500 | 100 | 500 | >500 | 100 | >500 |
| | pH 8.2 | 250 | >500 | >500 | >500 | >500 | >500 | >500 | >500 | >500 |
| (E) | pH 6.8 | 25 | >500 | 500 | >500 | 500 | >500 | >500 | >500 | 250 |
| | pH 8.2 | 250 | >500 | >500 | >500 | >500 | >500 | >500 | >500 | >500 |
| (F) | pH 6.8 | 100 | >500 | >500 | >500 | >500 | >500 | >500 | >500 | 100 |
| | pH 8.2 | 500 | >500 | >500 | >500 | >500 | >500 | >500 | >500 | 250 |
| (G) | pH 6.8 | 25 | >500 | 250 | 250 | 500 | 500 | 500 | 500 | 100 |
| | pH 8.2 | 250 | >500 | >500 | 500 | >500 | >500 | >500 | >500 | 250 |
| (H) | pH 6.8 | >500 | >500 | >500 | >500 | >500 | >500 | >500 | >500 | >500 |
| | pH 8.2 | >500 | >500 | >500 | >500 | >500 | >500 | >500 | >500 | >500 |
| (I) | pH 6.8 | <10 | >500 | >500 | 100 | 100 | >500 | 250 | 250 | 50 |

TABLE III-continued

Minimum Inhibitory Concentrations for Test Compounds in Bacteria Species (in ppm)

| Compound STANDARD I | ORGANISMS | | | | | | | | |
|---|---|---|---|---|---|---|---|---|---|
| | Bs | Ea | Ec | Kp | Pv | PRD | Pa | SC | Sa |
| pH 8.2 | 100 | >500 | >500 | >500 | >500 | >500 | >500 | >500 | >500 |
| (J) pH 6.8 | <10 | >500 | 100 | >500 | 250 | >500 | >500 | >500 | 25 |
| pH 8.2 | 50 | >500 | >500 | >500 | >500 | >500 | >500 | >500 | 100 |
| (K) pH 6.8 | <10 | >500 | >500 | >500 | 500 | >500 | >500 | >500 | >500 |
| pH 8.2 | 100 | >500 | >500 | >500 | >500 | >500 | >500 | >500 | >500 |

TABLE IV

Minimum Inhibitory Concentrations for Test Compounds in Yeast/Fungi Species (in ppm)

| COMPOUND | ORGANISMS | | | | | | |
|---|---|---|---|---|---|---|---|
| | An | Ca | PC | Sc | Tv | Ap | Fo |
| STANDARD | >500 | >500 | >500 | 500 | >500 | >500 | >500 |
| A | 25 | 25 | 25 | <10 | 25 | 25 | 25 |
| B | 25 | <10 | 25 | <10 | 25 | <10 | 25 |
| C | 10 | 10 | 25 | 10 | 25 | 10 | 10 |
| D | 10 | 10 | 25 | 10 | 25 | 10 | 10 |
| E | 50 | 25 | 25 | 25 | 100 | 25 | 50 |
| F | 250 | 250 | 250 | 250 | >500 | 100 | 500 |
| G | 100 | 50 | 100 | 50 | 250 | 50 | 100 |
| H | >500 | >500 | >500 | >500 | >500 | >500 | >500 |
| I | 25 | <10 | 25 | <10 | 25 | <10 | <10 |
| J | <10 | <10 | <10 | <10 | 25 | <10 | <10 |
| K | 25 | 25 | 25 | 25 | 25 | <10 | 25 |

Marine Antifouling Activity

The present invention is also directed to a method for inhibiting marine organisms. The term "marine organisms" is meant to include marine animals, such as barnacles, serpulid, bryozoa, oysters and hydroids, and marine plants, such as green algae and brown algae. The method for inhibiting marine organisms comprises contacting a surface exposed to a marine environment in which marine organisms grow with a marine antifouling effective amount of the compound of this invention.

As will be appreciated by those skilled in the art, not all of the compounds disclosed herein are active at the same concentrations or against the same marine organism species. That is, there may be some compound-to-compound variation in marine antifouling potency and spectrum of marine antifouling activity. Furthermore, a specific compound's marine antifouling activity may be dependent on the specific materials with which the compound is formulated to form a marine antifouling composition.

As used herein, the term "marine antifouling effective amount" refers to that amount of one or a mixture of two or more of the compounds of this invention needed to exhibit inhibition of selected marine organisms. Typically, this amount varies from providing about 1 weight percent to about 30 weight percent of the compound to a marine antifouling composition which is used to treat a surface exposed to a marine environment in which marine organisms live or grow. Such amounts vary depending upon the particular compound tested and marine organism to be treated. Also, the exact concentration of the compounds to be added in the preparation of industrial and consumer formulations may vary within a product type depending upon the components of the formulation.

A composition comprising a marine antifouling effective amount of the compound will also comprise an inert diluent which may be, for example, in the form of a paint. Particularly preferred are those paints having a vinyl resin binder such as, for example, a plasticized polyvinyl chloride or a polyvinyl chloride-polyvinyl acetate type. Preferably, the binders are formulated as latexes or emulsions. In a paint composition, the compound of the present invention is preferably used in an amount from about 1 to about 30 weight percent and, most preferably, from about 10 to about 25 weight percent. In addition to vinyl resin binder paints, epoxy and polyurethane binder paints containing the compound may also be useful. Coatings and films prepared from paints comprising the compound of the present invention typically remain substantially free from build-up of marine organisms for periods ranging from about 3 to about 12 months, depending upon the concentration of the compound and the thickness of the applied coating or film.

The term "a surface exposed to a marine environment" refers to a surface where a marine organism naturally or normally lives or grows. Typically, such a surface will be an area that is in continual or periodic contact with a marine environment such as an ocean or other body of water. Typical surfaces include, for example, a ship hull.

The marine antifouling activity of the compounds of the present invention is demonstrated by the following techniques.

Test panels are prepared from clear, rigid polyvinyl chloride film that is $0.381 \times 10^{-3}$ m thick and has one textured surface. The test panels are 0.1524 m by 0.1524 m squares that have 0.00635 m holes punched at corners on 0.127 m centers. A 0.102 square template, with a 0.067 m diameter hole at the center, is attached to the center of the textured surface of the test panels.

A candidate marine antifoulant compound (1.0 g) is stirred into a resinous latex binder (9.0 g). A portion of the compound/binder mixture (1.5 g) is added to the center of the test panel and uniformly spread over the circular area inside the template.

Water is added dropwise as needed to properly spread the compound/binder mixture. The template prevents the compound/binder mixture from spreading beyond the uncovered area. The test panel is allowed to sit for between ten to thirty minutes until the edge of the spread compound/binder mixture has dried. The template is then removed. The test panel is then allowed to dry for 8 to 12 hours at room temperature.

Two test panels are prepared for each candidate marine antifoulant compound. Two control test panels are also prepared by only treating with the resinous latex binder. One test panel of each candidate marine surfactant compound is attached over a white background to the topside of an exposure support apparatus. The second test panel is attached over a black background to the underside of the exposure support apparatus. The exposure support apparatus is placed horizontally 0.0254 m under a marine surface with the white background topside facing up. The exposure support apparatus is exposed to the marine environment for both 10 and 20 weeks during which time the control test panels become substantially covered with mature marine organism growth on both the topside and underside exposures.

After being removed from the exposure support apparatus, each test panel is inspected and rated for marine organism growth on both the treated and untreated areas of the test panel. The marine organisms present on the treated and untreated areas are noted. The presence of algae spores and bacterial slime are noted but not included in rating each test panel. The test panels are rated on a scale from 10 (representing completely free of marine organism growth) to 0 (representing completely covered with marine organism growth).

In Table V, the marine antifouling rating values for some of the compounds listed in Table I are set forth, as well as the ratings for control panels (using no marine antifouling compound, and referred to in Table V as "Control") and panels using a standard commercial marine antifouling compound (with copper (I) oxide ($Cu_2O$) as the active agent and referred to in Table V as "STANDARD II").

TABLE V

Marine Antifouling Rating for Test Compounds

| | Marine Antifouling Ratings | | | |
|---|---|---|---|---|
| | 10 Week Test | | 20 Week Test | |
| Compound | Top Panel | Bottom Panel | Top Panel | Bottom Panel |
| B | 10 | 4 | 1 | 1 |
| C | 7 | 1 | — | — |
| Control | 7 | 1 | 1 | 1 |
| STANDARD II | 9 | 1 | 3 | 3 |

What is claimed is:

1. A compound corresponding to the formula:

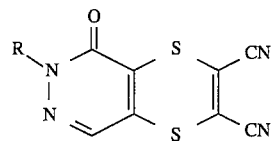

wherein R represents

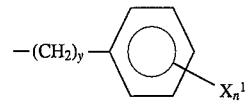

wherein $X^1$ is Cl, Br, $NO_2$ or $CH_3$, y is 0 or 1 and n is 0, 1 or 2.

2. The compound of claim 1 wherein R represents:

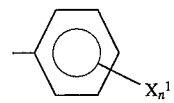

wherein $X^1$ is Cl and n is 0, 1, or 2; or $X^1$ is Br and n is 1; or $X^1$ is $NO_2$ and n is 1; or $X^1$ is $CH_3$ and n is 1; or wherein R represents:

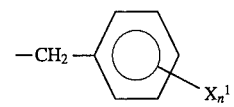

wherein $X^1$ is Cl and n is 0 or 1; or $X^1$ is $CH_3$ and n is 1.

3. An antimicrobial composition comprising an inert diluent and an antimicrobially-effective amount of a compound corresponding to the formula:

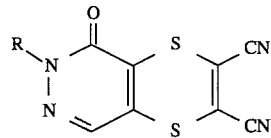

wherein R represents

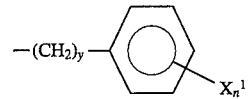

wherein $X^1$ is Cl, Br, $NO_2$ or $CH_3$, y is 0 or 1 and n is 0, 1 or 2.

4. The composition of claim 3 wherein R represents:

wherein $X^1$ is Cl and n is 0, 1, or 2; or $X^1$ is Br and n is 1; or $X^1$ is $NO_2$ and n is 1; or $X^1$ is $CH_3$ and n is 1; or wherein R represents:

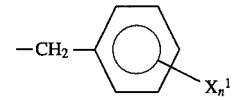

wherein $X^1$ is Cl and n is 0 or 1, or $X^1$ is $CH_3$ and n is 1.

5. The composition of claim 3 wherein the compound is present in an amount to provide from about 1 part per million to about 5,000 parts per million by weight of the compound to an antimicrobial habitat that is contacted with the composition.

6. A method for inhibiting microorganisms from the group consisting of bacteria, yeast, fungi, algae, and protozoa in a microbial habitat comprising contacting said microbial habitat with an antimicrobially-effective amount of a compound corresponding to the formula:

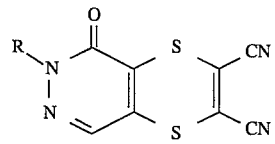

wherein R represents

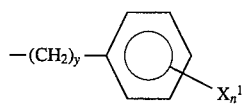

wherein $X^1$ is Cl, Br, $NO_2$ or $CH_3$, y is 0 or 1 and n is 0, 1 or 2.

7. The method of claim 6 wherein R represents:

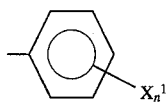

wherein $X^1$ is Cl and n is 0, 1, or 2; or $X^1$ is Br and n is 1; or $X^1$ is $NO_2$ and n is 1; or $X^1$ is $CH_3$ and n is 1; or wherein R represents:

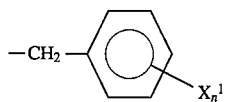

wherein $X^1$ is Cl and n is 0 or 1, or $X^1$ is $CH_3$ and n is 1.

8. The method of claim 6 wherein the compound is used in an amount to provide from about 1 part per million to about 5,000 parts per million by weight of the compound to a microbial habitat being contacted with composition comprising an inert diluent and the compound.

9. A method for preventing the growth of marine organisms on a surface exposed to a marine environment in which marine organisms grow comprising contacting said surface with a marine antifouling effective amount of a compound corresponding to the formula:

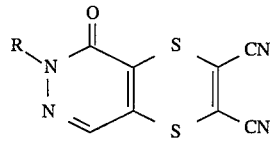

wherein R represents

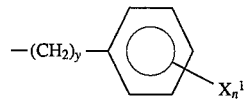

wherein $X^1$ is Cl, Br, $NO_2$ or $CH_3$, y is 0 or 1 and n is 0, 1 or 2.

10. The method of claim 9 wherein R represents:

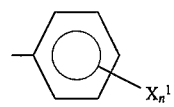

wherein $X^1$ is Cl and n is 0 or 1, or 2; or $X^1$ is Br and n is 1; or $X^1$ is $NO_2$ and n is 1; or $X^1$ is $CH_3$ and n is 1; or wherein R represents:

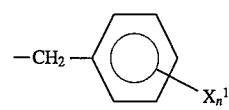

wherein $X^1$ is Cl and n is 0 or 1, or $X^1$ is $CH_3$ and n is 1.

11. The method of claim 9 wherein the compound is contacted with the surface in an amount from about 1 to about 30 weight percent of a composition comprising an inert diluent and the compound.

* * * * *